(12) United States Patent
Rollins et al.

(10) Patent No.: US 7,833,777 B2
(45) Date of Patent: Nov. 16, 2010

(54) STABILIZED ACTIVELY AERATED COMPOST TEA

(75) Inventors: Carole Ann Rollins, Sonoma, CA (US); James Eddington, Novato, CA (US); Elaine Ingham, Corvalis, OR (US)

(73) Assignee: Nature Technologies International LLC, Sonoma, CA (US)

( * ) Notice: Subject to any disclaimer, the term of this patent is extended or adjusted under 35 U.S.C. 154(b) by 1006 days.

(21) Appl. No.: 11/210,202

(22) Filed: Aug. 22, 2005

(65) Prior Publication Data

US 2007/0042486 A1  Feb. 22, 2007

(51) Int. Cl.
*C12N 1/20* (2006.01)
(52) U.S. Cl. .................................. 435/252.4; 435/243
(58) Field of Classification Search ................. 424/93.3; 435/252.4
See application file for complete search history.

(56) References Cited

U.S. PATENT DOCUMENTS

| | | | |
|---|---|---|---|
| 2,333,027 A | 10/1943 | Morgenthaler | |
| 3,120,439 A | 2/1964 | Reale | |
| 3,637,398 A | 1/1972 | Elerath | |
| 4,347,632 A | 9/1982 | Criss | |
| 4,384,877 A | 5/1983 | Nemetz | |
| 4,803,800 A | 2/1989 | Romaine | |
| 4,932,196 A | 6/1990 | Schnittjer | |
| 4,952,451 A | 8/1990 | Mueller | |
| 5,242,700 A | 9/1993 | Schlecht | |
| 5,283,059 A | 2/1994 | Suzuki | |
| 5,612,079 A | 3/1997 | Lunder | |
| 5,733,774 A | 3/1998 | Jin | |
| 6,168,949 B1 | 1/2001 | Rubenberger | |
| 6,352,855 B1 | 3/2002 | Kerouac | |
| 6,649,405 B2 | 11/2003 | Alms et al. | |
| 6,727,090 B1 | 4/2004 | Hronek | |
| 6,767,381 B2 | 7/2004 | Huhn | |
| 2002/0174697 A1 | 11/2002 | Reid et al. | |
| 2003/0068303 A1 | 4/2003 | Selvig et al. | |
| 2003/0072817 A1 | 4/2003 | Aoki | |
| 2003/0104076 A1 | 6/2003 | Berkulin et al. | |
| 2003/0113908 A1 | 6/2003 | Hussey | |
| 2003/0116648 A1 | 6/2003 | Schraven | |
| 2004/0096963 A1 | 5/2004 | Hahn | |
| 2004/0128852 A1 | 7/2004 | Joseph | |
| 2004/0161524 A1 | 8/2004 | Sakai et al. | |

FOREIGN PATENT DOCUMENTS

WO    WO 00/42164 A1    7/2000

OTHER PUBLICATIONS

Scheurell et al. "Compost tea as a container medium drench for suppressing seedling damping-off caused by *Pythium ultimum*". Phytopathology. 2004, 94: 1156-1163.*
Bess V.H. "Understanding compost tea". BioCycle. Oct. 2000, vol. 41, No. 10, pp. 71-72.*

* cited by examiner

*Primary Examiner*—Vera Afremova
(74) *Attorney, Agent, or Firm*—Bay Area Technology Law Group PC

(57) ABSTRACT

In combination, an aerobic microbial biomass and viability supporting container therefore. The aerobic microbial biomass is composed of microorganisms extracted from a tea composition and stored as a liquid or applied to a stabilizing medium for storage as a solid. The aerobic microbial biomass is stored in a container which is characterized as being oxygen permeable to the extent of maintaining at least approximately 5.5 ppm oxygen in the aerobic microbial biomass wherein less than approximately 10% of the microorganisms are maintained in an active state and over a period of at least twelve months, a minimum of at least 50% of the extracted microorganisms are maintained as viable.

9 Claims, No Drawings

STABILIZED ACTIVELY AERATED COMPOST TEA

TECHNICAL FIELD

The present invention relates to a plant protection and nutrient transformative medium which is capable of being maintained as viable in a dry or liquid state over an extended storage period and which can be applied to plant life as a significant plant protection mechanism, a nutrient transformative medium, and a soil building vehicle.

BACKGROUND OF THE INVENTION

The agricultural community has, for quite some time, shown great interest in compost teas as they can be used to address plant, foliar and root diseases as well as providing mechanisms for transforming nutrients for plants and their surrounding support media and enhancing the soil foodweb. Such teas offer these benefits through aerobic microorganisms which are introduced into an aqueous medium and extracted through aeration and agitation, the density of which is multiplied by introducing nutrient sources to the microorganism-containing teas.

The agricultural community, either through self policing or in addressing pressures placed upon it by governmental agencies and watch dog special interest groups, has felt the need to reduce or entirely eliminate certain pesticides and synthetic fertilizers which can often times foul water supplies and the surrounding eco systems. Not only are certain pesticides difficult to remove from edible crops but bird and other animal life can become sick and spread disease as a result of ingesting certain non-organic crop pesticides and synthetic fertilizers. As such, compost teas are being viewed more and more as primary plant protection, nutritional transformative mechanisms and soil enhancing and disease control supplements as they provide a natural and safe alternative to current widely employed practices.

Although there are a number of techniques for producing compost teas, they generally all include the use of a high quality compost which builds a complex microbiologically enhanced aqueous complex from which the organic species are extracted. For example, microorganism sources such as worm casting, compost, humus and leaf mold are added to a liquid medium which can also include the inoculation of bacteria, fungi, protozoa and nematodes and nutrient sources for the microorganisms. The beneficial microorganisms are then extracted from the liquid culturing medium through an aeration process in vessels filled with non-chlorine/chloramines pure water. Such techniques are well known to this art. In this regard, reference is made to U.S. Pat. Nos. 6,727,090 and 6,767,381 and the references cited therein, all of which are incorporated herein by reference.

In following the teachings of the prior art, various microorganisms are cultured in a liquid medium along with food for the microorganisms. The medium is actively aerated in vessels for 12, 24 or 36 hour periods to maintain dissolved oxygen levels above approximately 6.0 ppm throughout the entire process. The resulting liquid is decanted and stabilized or immediately applied to a dry mix for stabilization. Upon doing so, target levels of organism species, upon extraction are sought to be at least active bacteria (10 µg/ml), total bacteria (150 µg/ml), active fungi (2 µg/ml), total fungi (2 µg/ml), flagellates (1,000), amoeboe (1,000), ciliates (20), and nematodes (2).

Although, as noted previously, the use of compost teas in the agricultural industry is well known, their use is not without recognized limitations. Compost teas are traditionally maintained in a liquid state, applied as a soil drench, or sprayed on leaf and plant surfaces. In foliar applications, it is critical that the microorganisms be maintained in an active state. If most of the microorganisms are dormant, they will not adhere to the leaf surface. They must be in an active state when they reach the leaf surface to facilitate attachment to that surface. Maintaining viability of the microorganisms in aqueous media is difficult indeed. Suitable nutrients must be introduced and their levels maintained. Further, temperature and other environmental conditions must be considered while extended shelf life of such products is generally almost impossible to achieve.

It is thus an object of the present invention to provide a system for creating and maintaining an aerobic microbial biomass which can be maintained in a dry or liquid state for extended periods while maintaining its viability for future use as a plant protecting mechanism, a nutrient transformative medium and a soil enhancing vehicle.

It is yet a further object of the present invention to provide in combination an aerobic microbial biomass and viability supporting container wherein a relatively small percentage of microorganisms contained therein are maintained in an active state while a relatively high percentage of microorganisms are maintained as viable.

These and further objects will be more readily appreciated when considering the following disclosure and appended claims.

SUMMARY OF THE INVENTION

The present invention involves, in combination, an aerobic microbial biomass and viability supporting container therefore. The aerobic microbial biomass comprises microorganisms extracted from the tea composition and may be either employed in a liquid form or applied to a stabilizing medium. The aerobic microbial biomass is stored in a dry or liquid state in a container, the container characterized as being oxygen permeable to the extent of maintaining at least approximately 5.5 ppm oxygen in the aerobic microbial biomass wherein less than approximately 10% of the microorganisms are maintained in an active state and over a period of at least twelve months and a minimum of approximately 50% of the extracted microorganisms are maintained as viable.

DETAILED DESCRIPTION OF THE INVENTION

As noted previously, beneficial microorganisms are grown and nurtured in aqueous medium. It is the prime object of the present invention to provide such nutrients in an aqueous or dry stabilization medium for extended periods of time, noting that the dry stabilization medium would later be soluabilized for liquid application to plants and soil. Such stabilization medium is intended to include, but not limited to, food and nutrient sources for the microorganisms such as one or more members selected from the group consisting of oat, bran, dry molasses, aloe, quinoa, spelt, rye, barley, wheat, soy, rice, alfalfa, milk powder, egg whites, kelp, humic acid, hydrolyzed fish, spirulina, algae, sugar, honey and date powder. Ideally, the tea liquid medium made the subject of microorganism culturing, is applied to a stabilization medium in an amount of approximately 4 ounces of liquid for every 32 ounces of the dry stabilization medium. This mixture is then air dried for 14 days to a moisture content of approximately 10-30 weight percent.

It is an object of the present invention to produce an aqueous or dry microorganism-containing medium or solid. The dry microorganism-containing solid is produced by first mixing the aqueous culturing medium to the above-described stabilization medium in a process of addition, remixing and drying. Ideally, liquid is added to the stabilization medium by spraying the liquid onto the medium periodically. For example, the dry stabilization medium can be placed in a tumble mixer whereupon the tea is sprayed within the mixer three times over a 24 hour period noting that between spray additions, the stabilization medium is dried through tumbling supplemented by the introduction of blown air at a temperature not exceeding 70° F. in order to protect the microorganisms. The combination of microorganisms and stabilization medium is dried to a moisture content of approximately 10-30 weight percent.

In performing the aqueous microorganism addition to the stabilization medium, care must be taken to preserve the integrity of the microorganisms which are recognized as being somewhat fragile. In this regard, impellor pumps are to be avoided in making the microorganism addition. If pumps are employed, only diaphragm pumps should be employed as the beneficial fungi have long hyphae which can easily be sheared by impellor pumps. Venturi Foggers are a preferred mechanism for introducing the aqueous microorganism based liquid to the stabilization medium as they are gentle on the microorganisms producing droplets from approximately 8.5 to 30 microns in size. Fans can be employed to move the fog to the surface of the stabilization medium which is mixed within the medium upon tumbling.

As noted previously, although the benefits of compost teas have been widely recognized, long term storage and viability issues have remained nagging limitations. Teas of the prior art maintained as liquids or solids develop aerobic conditions when deprived of oxygen during storage. If this occurs, pathogen populations increase comprising the viability of the microorganisms and thus their commercial use.

Significantly, it has been determined that the viability of the present microorganism-containing teas can be maintained for extended periods in a liquid or dry state alone or in a stabilizing medium if a suitable container is employed. The container, to be useful in the practice of the present invention, must be oxygen permeable to the extent of maintaining at least approximately 5.5 ppm oxygen in the aerobic microbial biomass that comprises microorganism-containing tea in an aqueous medium or the combination microorganism-containing tea and stabilization medium. The biomass is maintained in a liquid or dry state wherein less than approximately 10% of the microorganisms are maintained in an active state in over a period of at least twelve months having a minimum of approximately 50% of the extracted microorganisms maintained as viable. By having at least 90% of the microorganisms maintained in an inactive state, nutritional requirements of the aerobic microbial biomass are minimal. By maintaining at least approximately 5.5 ppm oxygen, pathogen degradation of the nutrient biomass is checked and controlled.

A prime example of a suitable breathable container is one produced from low density polyethylene, cast nylon or nylon coex. Such material has been available as storage bags for produce, meats and dry food products noting that for use herein, ideally, such storage bags should possess a moisture vapor transmission rate, also known as water vapor transmission rate of approximately 1.2 μg/ml per 100 square inches per 24 hours at a 100° F. at 100% relative humidity per ASTM E-96. These bags should also have gas transmission rates expressed in cubic centimeters per mil per 100 square inches of film per 24 hours at 73° F. and 0% relative humidity per ASTM E-1434 of approximately 494-5,000 $CO_2$ and 250-840 $O_2$.

The aerobic microbial biomass can be stored for extended periods while maintaining its viability. When appropriate, the solid medium can be applied directly as a top dressing or as a planting mix. The aerobic microbial biomass could also be added in aqueous or solid form to mulch or compost which, in turn, could also be employed as a top dressing or planting mix. When added to a compost piles, it can function as inoculums. Ideally, the solid form of aerobic microbial biomass is stored as a fine powder having a particle size of approximately 200 to 1000 microns. This powder effectively mixes well with water and can be thus converted to a liquid form at time of application for developing a liquid to be applied through irrigation systems or as spray for soil drenching as well as a foliar spray for leaves, trunks and stems.

The invention claimed is:

1. A system for creating and maintaining an aerobic microbial biomass comprising said aerobic microbial biomass and a viability supporting container, wherein said aerobic microbial biomass comprises a liquid tea composition including microorganisms and a culturing medium for said microorganisms stored in said container, wherein said container is characterized as being oxygen permeable to the extent of maintaining at least approximately 5.5 ppm oxygen in said aerobic microbial biomass, and wherein less than approximately 10% of said microorganisms are maintained in an active state and over a period of at least twelve months and a minimum of approximately 50% of said microorganisms are maintained as viable.

2. The combination of claim 1 wherein said culturing medium contains at least one member selected from the group consisting of worm castings, compost, humus and leaf mold.

3. The system of claim 2 wherein said culturing medium further comprises protozoa and nematodes.

4. The system of claim 1 wherein said biomass is characterized as having approximately at least 10 μg/ml active bacteria, 150 μg/ml total bacteria, 2 μg/ml active fungi, 2 μg/ml total fungi, 1000 flagellates, 1000 amoeboe, 20 ciliates and 2 nematodes.

5. The system of claim 1 further comprising a nutrient source for said microorganisms.

6. The system of claim 5 wherein said nutrient source comprises at least one member selected from the group consisting of oat, bran, dry molasses, aloe, guinoa, spelt, barley, wheat, soy, rice, alfalfa, milk powder, egg whites, kelp, humic acid, hydrolyzed fish, spirulina, algae, sugar, honey, and date powder.

7. The system of claim 1 wherein said viability supporting container comprises a member selected from the group consisting of cast nylon, nylon coex and low density polyethylene bags.

8. The system of claim 7 wherein said viability supporting containers are characterized as having a moisture vapor transmission rate of approximately 1.2 g/ml/100 $in^2$/24 hrs. at 100° F. and 90% relative humidity.

9. The system of claim 7 wherein said viability supporting container comprises a low density polyethylene bag characterized as having a gas transmission rate of approximately 250 to 840 cc $O_2$ and approximately 495-5000 cc $CO_2$/ml/100 $in^2$/24 hrs. measured at 73° F. and 0% relative humidity.

* * * * *